| United States Patent [19] | [11] Patent Number: 5,059,622 |
| Sears | [45] Date of Patent: Oct. 22, 1991 |

[54] METHOD FOR REDUCING BLOOD PRESSURE LEVELS IN HYPERTENSIVE PERSONS

[75] Inventor: Barry D. Sears, Swampscott, Mass.

[73] Assignee: BioSyn, Inc., Marblehead, Mass.

[21] Appl. No.: 539,384

[22] Filed: Jun. 18, 1990

Related U.S. Application Data

[60] Division of Ser. No. 400,288, Aug. 29, 1989, abandoned, which is a continuation-in-part of Ser. No. 251,139, Sep. 28, 1988, abandoned.

[51] Int. Cl.$^5$ .................... A61K 31/22; A61K 31/20; A61K 31/23
[52] U.S. Cl. .................... 514/549; 514/552; 514/560
[58] Field of Search ............. 514/552, 560, 558, 549

[56] References Cited

U.S. PATENT DOCUMENTS 4,681,896  7/1987  Horrobin .................... 514/560
4,920,098  4/1990  Cotter et al. ................ 514/558

*Primary Examiner*—Frederick E. Waddell
*Assistant Examiner*—Raymond J. Henley, III
*Attorney, Agent, or Firm*—Richard P. Crowley

[57] ABSTRACT

The modulation of prostaglandin levels can be realized through the dietary intake of specified ratios of activated Omega 6 essentially fatty acids when combined with the appropriate amount of eicosapentaenoic acid (EPA), an Omega 3 fatty acid. The modulation of prostaglandins levels can be determined by changes in physiological parameters which are related to prostaglandin levels in mammals. Certain ratios of activated Omega 6 essentially fatty acids and EPA can have significant physiological benefits, whereas other ratios demonstrate detrimental physiological effects in mammals.

8 Claims, 1 Drawing Sheet

METHOD FOR REDUCING BLOOD PRESSURE LEVELS IN HYPERTENSIVE PERSONS

REFERENCE TO PRIOR APPLICATIONS

This application is a divisional application of Ser. No. 07/400,288, filed Aug. 29, 1989, now abandoned which application is a continuation-in-part of Ser. No. 07/251,139, filed Sept. 28, 1988, now abandoned.

FIELD OF THE INVENTION

The present invention relates to both food products and pharmaceutical compositions containing specified activated Omega 6 essential fatty acids, gamma linolenic acid (GLA) and/or dihomo gamma linolenic acid (DGLA) combined with eicosapentaenoic acid (EPA), for the modulation of prostaglandin levels in mammals. Certain ratios of activated Omega 6 essential fatty acids and EPA successfully modulate the levels of beneficial prostaglandins that can provide effective treatment for existing disease states, or can be used as a prophylactic approach to prevent the onset of disease states such as cardiovascular disease and immune disorders. On the other hand, other ratios of the same fatty acids have a deleterious effect on existing disease conditions by increasing the levels of detrimental prostaglandins, and would be considered counterproductive in the treatment or prevention of disease states.

BACKGROUND OF THE INVENTION

Prostaglandins are a group of hormone like substances which are known to play a significant factor in virtually all body function. In particular, prostaglandins play important roles in controlling the cardiovascular and immunological systems of the human body. Yet as important are prostaglandins for human health, their production is totally dependent on the dietary intake of a specialized group of fatty acids known as essential fatty acids. Essential fatty acids cannot be made by the human body, and must be supplied in the diet to provide sufficient precursors from which to synthesize prostaglandins. The primary essential fatty acids belong to the Omega 6 family of essential fatty acids. The complexity and dynamics of the transformation of these Omega 6 essential fatty acids into prostaglandins is shown in FIG. 1.

The complexity of Omega 6 essential fatty acid metabolism, and thus the determination of which prostaglandins are produced, is due to the activity of various enzymes responsible for the biological transformation of these essential fatty acids. Differences in the enzyme activity control the relative levels of the true prostaglandin precursors: dihomo gamma linolenic acid (DGLA) and arachidonic acid (AA). The prostaglandins of the one series derived from DGLA are beneficial for the cardiovascular system, stimulate the immune system, and control hormone synthesis and release. On the other hand, the prostaglandins of the two series derived from AA can inhibit cardiovascular function, depress the immune system, and generally have diametrically opposed physiological functions to prostaglandins of the one series. To maintain proper body function, both series one and two prostaglandins must be formed. Therefore, it is the balance of DGLA to AA in each body's cell that eventually determines the exact ratio of the one and two series prostaglandins that are formed. An overabundance of either the one or two series prostaglandins is not consistent with optimal physiological performance. The ratio of DGLA to AA is ultimately determined by the two primary enzymes that control the ratio of DGLA and AA in each cell. These two enzymes are delta-6 desaturase (D6D) and delta-5 desaturase (D5D).

The enzymes D6D and D5D are the rate controlling factors which determine the amounts of each of the prostaglandin precursors which will ultimately give rise to one series prostaglandins or two series prostaglandins. This becomes a primary factor for the treatment and possible prevention of cardiovascular disorders as the prostaglandins derived from AA (especially thromboxane $A_2$) are considered to be the primary cause of cardiovascular disease[1], whereas prostaglandins derived from DGLA (especially $PGE_1$) are considered to be important in reducing the probability of developing cardiovascular disease.[2] Likewise, certain prostaglandins derived from AA (such as $PGE_2$ and thromboxane $A_2$) suppress the immune system, while prostaglandins from DGLA (such as $PGE_1$) stimulate the immune system. Prostaglandins are also be formed from eicosapentaenoic acid (EPA). However, compared to the powerful physiological actions of prostaglandins of the one and two series, those derived from EPA are relatively neuter in theirphysiological actions.

Because EPA is a prevalent constituent in certain diets such as the Greenland Eskimos, and since the Greenland Eskimos have a very low incidence of cardiovascular disease, it has been assumed that EPA can treat or provide prophylaxis against various aspects of cardiovascular disease. This has been disclosed in British Patent Nos. 1,604,554 and 2,033,745.

Likewise, prior art has recognized the beneficial effects of GLA and/or DGLA as a treatment for cardiovascular disease in German Patent No. 2,749,492 and even earlier prior art concerning GLA in British Patent No. 1,082,624.

The use of a combination of many Omega 6 fatty acids with EPA and other Omega 3 fatty acids (i.e. docosahexanoic acid or DHA) which are not direct precursors for prostaglandin synthesis was disclosed in U.S. Pat. No. 4,526,902. However, this particular patent teaches that the roles of EPA and another fatty acid docsahexaenoic acid (DHA) are to compete with AA for various enzymes (i.e. cyclooxygenase) important in the production of prostaglandins, thereby leading to the inhibition of series two prostaglandins. This art does not refer to the critical role of EPA alone in its inhibitory action of the D5D enzyme. This prior art also makes the assertion that all Omega 6 fatty acids such as linoleic acid, GLA, and DGLA are biologically equivalent in terms of producing prostaglandins of the one series, and in particular $PGE_1$.

It has been shown that in human adipose tissue (the primary storage site of fat) the ratio of linoleic acid to GLA to DGLA is approximately 100:2:1.[3] The reason for such a radically altered ratio of Omega 6 fatty acids is their increased biological potency beyond the enzymatic step catalyzed by the enzyme delta-6-desaturase in the conversion of linoleic acid into GLA (see FIG. 1). As an example, it has been estimated that GLA was 163 times more effective in lowering cholesterol levels in humans than an equivalent dose of linoleic acid.[4] Likewise, studies in primates have indicated that DGLA has twice the biological potency of GLA in terms of reducing platelet aggregation which is mediated by the formation of $PGE_1$.[5] Furthermore, there is strong evidence that with increasing age the body's ability to produce GLA from linoleic acid is highly compromised therefore making the assertion of the equivalence of all Omega 6 fatty acids even more unlikely.[6,7] These results of biological potency corresponds well with the actual levels of Omega 6 fatty acids found in humans. What this means is that to assume that all Omega 6 fatty acids have the same biological potency in terms of prostaglandin production would be to grossly skew the balance of GLA and DGLA to EPA required to optimize prostaglandin levels of the one and two series prostaglandins.

U.S. Pat. No. 4,681,896 has taught that combinations of activated Omega 6 fatty acids with combinations of Omega 3 fatty acids are useful in the treatment of atopic disorders. Although this patent discloses "that the presence of n-3 fatty acids in a combination will lead to some inhibition of the conversion of DGLA to arachidonic acid by the delta-5-desaturase", the patent does not disclose that certain weight combinations of activated Omega 6 fatty acids and Omega 3 fatty acids (i.e. EPA) would be benefical, whereas other weight combinations are harmful to humans. Likewise, it is not taught in the general literature that certain weight combinations of activated Omega 6 essential fatty acids (such as GLA or DGLA) in combination with EPA would be beneficial, whereas other weight combinations would be detrimental.

The reason why prior art has not discovered this critical aspect of essential fatty metabolism is that no long term human studies have been conducted with combinations of activated Omega 6 essential fatty acids and EPA. This is important since the conversion of DGLA to AA in humans is relatively slow, yet proceeds continuously.[8] This slow conversion of DGLA into AA can be exceptionally harmful. The studies described in this patent illustrates deficiencies in the prior art.

SUMMARY OF THE INVENTION

It is the object of this invention to eliminate the above discussed deficiencies in the prior art and to improve upon the prior art.

It is also an object of this invention to demonstrate that activated Omega 6 essential fatty acids in combination with EPA composition create superior therapeutic benefits and thus a superior prophylatic composition compared to prior art in the form of pharmaceutical formulations or as food products.

The basis of this invention is the use of the appropriate EPA weight amount in relation to the amount of activated Omega 6 essential fatty acids to control or modulate the rate of transformation of DGLA into AA. Although the rate of transformation of DGLA in AA is relatively slow in man compared to other animal species[8], the long term benefits of supplementation with GLA or DGLA as disclosed in prior art(Brit. Patent No. 1,082,624) would be highly diminished as the increased levels of GLA or DGLA would simply eventually increase the levels of AA and thus increase the levels of prostaglandins of the two series being formed (see FIG. 1). Since the goal of this invention is to reduce such levels of prostaglandins derived from AA, while simultaneously increasing the production of prostaglandins from DGLA, the prior art concerning supplementation with GLA and DGLA alone would be counterproductive to the present invention.

EPA, but not other Omega 3 fatty acids (such as DHA) will inhibit this transformation of DGLA into AA in rats.[9] This has been shown in animals experiments using fish oil which contained both EPA and DHA and vegetable oil containing GLA. The GLA is readily metabolized into DGLA. However, the futher metabolism of DGLA and its transformation into AA was reduced. This reduction was only correlated with the amount of EPA, and there was no correlation with the presence of DHA.[9] This result is in accord with EPA acting as an inhibitor of D5D, whereas DHA does not. This in not taught in the prior art (U.S. Pat. No. 4,526,902) in which levels of DHA are considered important to that invention. The inhibitory effect of EPA on D5D by reducing the transformation of DGLA into AA will thereby increase the levels of precursors of the one series prostaglandins and simultaneously reduce the levels of the two series of prostaglandins. In this respect, the preferred combination of GLA and/or DGLA with EPA will have a much more selective effect on the modulation of prostaglandin levels than the prior art. Also, the preferred combinations of GLA and/or DGLA with EPA when compared to commonly used pharmaceuticals such as aspirin, corticosteroids, and anti-inflammatory drugs, such as ibuprofen and others, whose mode of action is to modulate prostaglandin levels by inhibiting the formation of all prostaglandins including the beneficial prostaglandins from the one series. The present invention will have a more selective benefit on the modulation of prostaglandin levels. Furthermore, preferred combinations of GLA and/or DGLA when combined with EPA will be more effective than disclosed in the above mentioned prior art. In fact, those combinations outside the weight ratios in this invention are detrimental to the health of mammals.

I have found that using a composition of GLA and/or DGLA in combination with EPA, provides substantial relief of existing cardiovascular and immune conditions. The preferred weight ratio of GLA and/or DGLA to EPA in the present invention is preferably 1:8. While these ratios are the preferred ratios, the ratio of GLA and/or DGLA to EPA may vary from 1:2 to 1:40.

The preferred physical form of the GLA, DGLA, and EPA would be as triglycerides, although other acceptable forms would include methyl or ethyl esters, monoglycerides, free fatty acids, or the appropriate salts of free fatty acids.

The preferred route of administration for the invention as a pharmaceutical would be orally as a capsule or tablet, although other routes of administration such as parenteral (intravenous, subcutaneous, and intramuscular), rectal, vaginal, buccal, and transdermal are feasible if the invention is formulated in such a manner to be successfully absorbed and utilized. As an example for parenteral administration, the perferred form would be as an emulsion with the knowledge that the ingredients of the emulsion must be physiologically compatible.

Given the critical importance of precise ratios of GLA and/or DGLA and EPA, as part of a mammal's dietary intake, on can also incorporate the invention in food products such as cooking oils, salad dressings, dairy products, emulsions, margarines, mayonnsaie, and other foods which can accomodate such fatty acids. Furthermore, microencapsulation, using standard technology, can produce a granulated version of the invention. With such granulated versions, it is also possible to introduce the invention in an even wider variety of food products in which such granulated powders can be incorporated.

If triglycerides are used, then they must meet the basic technical specifications set by the World Health Organization in the Codex Alimentarius.[10] A further requirement for the EPA component is that it should be as low in cholesterol content as possible, and be free of high levels of excessive levels or Vitamins A and D. The decreased levels of Vitamins A and D eliminate the possibility of potentially toxic amounts of Vitamins A and D given with the invention. The reasons for the low cholesterol levels are two fold. First is the need for the reduced intake of dietary cholesterol which would be contraindicated for cardiovascular treatment and prophylaxis. The second reason is that the removal of cholesterol from EPA source also removes other contaminants commonly found in EPA sources such as PCB's. It has been shown that traditional methods of vegetable oil refining do not remove PCB's.[11] Furthermore, the use of high temperatures and high vacuum to remove pesticides and herbicides from vegetable oils, will cause extensive isomerization of the double bonds of EPA thereby rendering it ineffective as an inhibitor for D5D. Therefore, if one is using triglycerides containing EPA, the preferred final refining technique before inclusion into the invention will be the removal of PCB's without isomerization of the double bonds. This can be accomplished through the use of molecular distillation, supercritical fluid extraction, or other such techniques skilled to those in the art.

DESCRIPTION OF THE INVENTION

The invention consists of a defined combination of essential fatty acids containing GLA and/or DGLA with the appropriate weight amount of EPA to modulate precursor pools for prostaglandin production in mammals. Therefore, to fully describe the invention one must illustrate general methods of GLA, DGLA, and EPA preparation.

GLA in the triglyceride form can be most easily extracted and refined from vegetable seed sources using standard technology common in the edible oil industry to create an oil suitable for human consumption as defined by international standards.[11] Common sources of GLA would include borage, black current, evening primrose seeds and oat bran. Certain microorganisms can also be fermented to produce GLA in the triglyceride form which can likewise be refined to meet international standards established for an edible oil.

GLA isolated in the triglyceride form can be chemically or biochemically transformed into free fatty acids, salts of free fatty acids, methyl or ethyl esters, or monoglycerides which can be further fractionated by standard techniques into fractions with higher GLA content than found in the starting oils. Finally, GLA can be chemically synthesized by standard chemical techniques.

A good natural source DGLA does not exit, so that to make this essential fatty acid, one must either elongate the free fatty acid, methyl or ethyl esters of GLA using standard techniques such as the malonic ester synthesis or to chemically synthesize the compound.

Like GLA, EPA can be easily extracted from natural sources such as plankton, krill, or marine animals. Also like GLA, EPA can be fermented under controlled conditions. In both cases, the extracted oil should be refined to meet all international standards for edible oils.

Again like GLA, the triglyceride form of EPA can be altered either by chemical or biochemical means to produce free fatty acids, salts of free fatty acids, methyl or ethyl esters, or monoglycerides which can be further fractionated to give higher EPA contents than the starting oil in the triglyceride form. EPA can also be chemically synthesized.

For the purpose of illustration only, the invention will be described in connection with the method of preparation in various pharmaceutical and food products and its use in the treatment in certain cardiovascular and immune disorders and hence by extension, its use in the prophylaxis of such cardiovascular and immune disorders. However, it is recognized that various changes and modifications to the illustrated examples can be made by those persons skilled in the art, all falling within the spirit and scope of the invention.

FIG. 1 describes the biochemical relationships of GLA and EPA that is important in the modulation of prostaglandins. It is the effect of EPA as an inhibitior of the enzyme delta 5 desaturase that diverts the flow of GLA into dihomo gamma linolenic acid (DGLA) instead of its further metabolism into arachidonic acid (AA). As shown in the examples of the invention, the ratio of EPA to GLA is critically important in the successful modulation of prostaglandins.

DESCRIPTION OF THE EMBODIMENTS

Example 1

Figure 1:
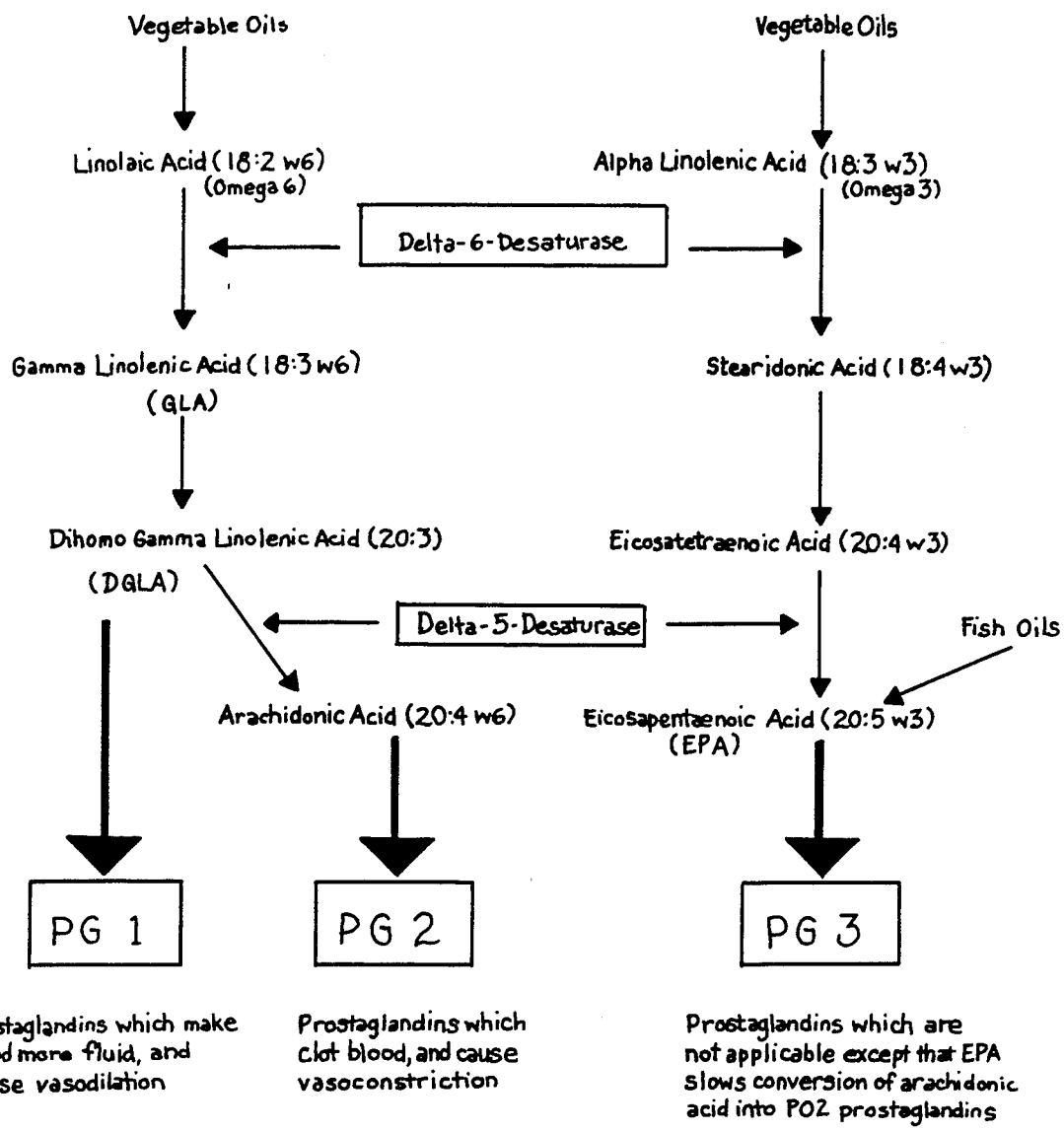

Six hypertensive subjects with an average blood pressure of 150/92 were placed on a daily intake of 80 mg. of GLA and 640 mg. of EPA per day for 6 weeks. At the end of six weeks, their blood pressure was measured and was lowered to an average of 134/78. Their intake was then changed to 80 mg. GLA and 320 mg. EPA per day for another 2 weeks. At the end of this period, their blood pressure was measured and the average was found to be 140/83. Their intake was then changed to 80 mg. GLA and 160 mg. EPA per day for another 2 weeks. At the end of this 2 week period, their blood pressure was measured, and the average blood pressure was 146/88. Their intake was then changed to 80 mg. GLA and 80 mg. EPA for another 2 weeks. At the end of this period, their blood pressure was measured, and the average blood pressure reading was 156/95. Their intake was changed to 80 mg. GLA and 40 mg. EPA per day for another another 2 weeks. At the end of 2 weeks, their blood pressure was measured, and found to average 162/100. At this point they were switched back to 80 mg. GLA and 640 mg. EPA for a final 2 weeks. The average blood pressure was reduced to 143/85. The results concerning the cardiovascular effects of different GLA and EPA ratios are shown in Table 1.

TABLE 1

| Effect of combinations of activated Omega 6 essential fatty acids and EPA on blood pressure in hypertensive individuals | | |
|---|---|---|
| Weeks | Ratio of EPA to GLA | Average Blood Pressure |
| Start | None | 150/92 |
| 6 | 8:1 | 134/78 |
| 2 | 4:1 | 140/83 |
| 2 | 2:1 | 146/88 |
| 2 | 1:1 | 156/95 |
| 2 | 0.5:1 | 162/100 |
| 2 | 8:1 | 143/85 |

These results show that some ratios of EPA and GLA are beneficial in the treatment of existing hypertension, whereas other ratios are detrimental to the existing disease condition.

Example 2

36 healthy adults were split into 6 groups of 6 individuals. They were given the following amounts of dietary supplements for 6 weeks on a daily basis.
Group 1: 80 mg. GLA and 3200 mg. EPA.
Group 2: 80 mg. GLA and 1600 mg. EPA.
Group 3: 80 mg. GLA and 800 mg. EPA.
Group 4: 80 mg. GLA and 400 mg. EPA.
Group 5: 80 mg. GLA and 80 mg. EPA.
Group 6: 80 mg. GLA and 40 mg. EPA.

At the end of 6 weeks, each individual was asked to evaluate their energy levels, digestive system responses, and skin condition based on the various levels of supplementation on a subjective scale comparing the initial starting point to the final point at the end of the study.

The following questions were asked, and the individuals were asked to respond using a grading system ranging from +2 (significantly improved), +1 (somewhat improved), 0 (no change), −1 (somewhat worse), −2 (significantly worse).
Question 1. Where your energy levels altered during the study?
Question 2. Did your stool composition change during the study?
Question 3. Was your skin condition altered during the study?

Each of these questions was used to assess physiological function which is closely related to prostaglandin formation, and therefore serves as an indication as to how dietary supplementation with activated Omega 6 essential fatty acids and EPA could effect prostaglandin formation, and therefore utlimately physiological function.

Energy levels are related to fatigue. Prostaglandins derived from AA (such as thromboxane $A_2$) are powerful vasoconstrictors that restrict the size of the capillary bed, and ultimately reduce the transfer rate of oxygen to muscle tissue. This lack of oxygen transfer will increase the levels of lactic acid in the muscle which causes fatigue. On the other hand, prostaglandins derived from DGLA (such as $PGE_1$) are powerful vasodilators which will increase the size of the capillary bed, thereby increasing oxygen transfer to muscle cells. However, if too much $PGE_1$ is formed, the kidneys will undergo a corresponding increase in vasodilation resulting in increased urination, and subsequent electrolyte depletion. The electrolyte depletion will contribution to fatigue, thereby decreasing energy levels. Therefore, at either extreme of the DGLA to AA ratio in the cardiovascular system, fatigue is the end result. However, at the optimal balance of these two fatty acids, energy levels should increase. Therefore, the levels of DGLA to AA in the cardiovascular system will determine which prostaglandins are eventually produced, and thus ultimately determine the energy level of the individual.

Likewise, stool composition is a good indicator of prostaglandin formation in the gastrointesintal tract. Vasoconstrictors such as thromboxane $A_2$ derived from AA will decrease the flow of water into the colon causing constipation. On the other hand, vasodilators such as $PGE_1$ derived from DGLA will increase the flow of water into the colon. If too much AA is formed by dietary supplementation with activated Omega 6 essential fatty acids and an insufficient amount of EPA, then an individual will develop constipation. On the other hand, if too much DGLA is being formed, then an individual will develop diarrhea. Again the appropriate balance of DGLA to AA is reflected in the stool composition. Thus the ratio of DGLA to AA in the mucosa that lines the gastrointensinal tract will determine which prostaglandins are ultimately produced which are reflected in the stool composition.

Finally, the skin also responds to changes in the DGLA to AA ratio which will manifest itself in the modulation of prostaglandins. Prostaglandins such as $PGE_2$ derived from AA are pro-inflammatory and will increase existing skin disorders such as eczema or produce dry skin. Furthermore, another group of prostaglandins known as leukotrienes produced from AA which are a major factor in the promotion of inflammatory response and allergies. On the other hand, prostaglandins produced from DGLA such as $PGE_1$ are anti-inflammatory and tend to reduce skin disorders. Moreover, leukotrienes cannot be formed from DGLA, so that their levels will also be modulated by the ratio of DGLA to AA in the skin. Therefore, the ratio of DGLA to AA in the skin will determine which prostaglandins are ultimately produced.

In Table 2 is shown the results of this study with the six groups of individuals using different ratios of activated Omega 6 essential fatty acids and EPA.

TABLE 2

Effect of weight ratios of activated Omega 6 essential fatty acids and EPA on physiological responses related to prostaglandin formation

| Group | EPA/GLA Ratio | Energy | Stool | Skin |
|---|---|---|---|---|
| 1 | 40:1 | −1.5 ± 0.2 | −1.3 ± 0.2 | +1.5 ± 0.2 |
| 2 | 20:1 | +0.8 ± 0.3 | −0.2 ± 0.3 | +1.3 ± 0.2 |
| 3 | 10:1 | +1.8 ± 0.2 | +1.5 ± 0.2 | +0.5 ± 0.2 |
| 4 | 5:1 | +1.2 ± 0.2 | +0.7 ± 0.3 | +0.7 ± 0.2 |
| 5 | 1:1 | −1.2 ± 0.3 | −1.7 ± 0.3 | −0.8 ± 0.3 |
| 6 | 0.5:1 | −1.7 ± 0.2 | −1.7 ± 0.3 | −1.3 ± 0.2 |

This data shows a number of results. At high ratios of EPA to GLA, energy levels and stool composition (due to diarrhea) worsened for the individuals at the end of the study compared to the start. Both results can be explained by excessive vasodilation caused by too much DGLA formation without a compensating production of AA to maintain an appropriate DGLA to AA balance in the cardiovascular system and gastrointensinal tract. On the other hand, their skin condition improved. This is because the skin is not as senistive to high DGLA levels as are the other systems. Thus at high EPA to GLA weight ratios there are some benefits, although many negative effects are also observed.

The ratio of 10:1 EPA to GLA in this study produced optimal results in the improvement of all three areas (i.e. energy, stool composition and skin).

At the lowest ratios of EPA to GLA, a distinct decrease in the energy, stool composition (due to constipation) and the skin composition (dryness and flaring up of eczema, if an existing condition prior to supplementation) were observed. All of these effects can be explained by the increased levels of AA formation giving rise to a decreased DGLA to AA ratio in these body tissues. Correspondingly, the lowered DGLA to AA ratio would lead to increased levels of vasoconstrictors and pro-inflammatory prostaglandins which adversely effect these physiological functions.

These results indicate that there is a specific range of activated Omega 6 essential fatty acids and EPA weight ratios that modulate prostaglandin levels to the benefit of humans, whereas other ratios actually decrease the individual's health. It should be noted that the ratios of activated Omega 6 essential fatty acids and EPA disclosed in the examples of prior art (U.S. Pat. No. 4,681,896) would have caused detrimental effects if given to patients with atopic disorders.

Example 3

6 patients with clinical manifestations of rheumatoid arthritis were place on a daily regimen of 480 mg. EPA and 120 mg. of GLA for three months. At the end of the time period, all clinical signs of rheumatoid arthritis were significantly diminished by joint pain as assessed by their physician and self assessment. This reduction is joint pain can be related to formation of prostaglandins which are anti-inflammatory, and the simultaneous suppression of prostaglandins which are pro-inflammatory.

Example 4

10 normal subjects were placed on a daily dose of 640 mg. EPA and 80 mg. GLA for 2 weeks. Blood samples were taken, the platelets were isolated. Measurements aggregation of platelets were taken before and after the supplementation program. In these platelet aggregation studies, the isolated platelets were stimulated with collagen (0.5 ug/ml) and a thromboxane $A_2$ analog (U46619) {500 ng/ml}. The results are shown in Table 3.

TABLE 3

Effects of EPA and activated Omega 6 essential fatty acids on platelet aggregation.

| Parameter | Average Before Supplementation | Average after Supplementation | p |
|---|---|---|---|
| Aggregation with U46619 | 117 ± 18 | 88 ± 27 | <0.01 |
| Aggregation lag with collagen* | 66 ± 23 | 79 ± 36 | <0.05 | n.s. not statistically significant
*lag time in seconds before aggregation

These results can be summarized as follows: There was no change in the platelet count, but there was a statistically significant decrease in platelet aggregation times. This indicates that the decrease in platelet aggregation was due to modulation of prostaglandins in the platelets by the dietary supplementation with EPA and GLA. This modulation of prostaglandins decreased the tendency of these platelets to aggregate when stimulated by an external response.

Example 5

A 0.5 gram soft gelatin capsule containing 15 mg. GLA and 60 mg. EPA. The number of capsules taken on a daily basis to modulate prostaglandins on a short term basis (up to 30 days) would be 4 capsules per day. The amount ingested for a long term basis would be one capsule per day as less activated Omega 6 essential fatty acids are required to maintain the tissue levels of DGLA to AA once they are established.

Example 6

To illustrate the effect of the invention for the treatment of immune disorders, an AIDS patient with clinicial signs of Karposi's sarcoma was put on a dialy regime of 8 0.5 gram soft gelatin capsules containing 15 mg. GLA and 60 mg. of EPA for 60 days. After 60 days, the dosage was increased to 16 capsules per day for the next 6 months. Three months after starting the program, the lesions associated with Karposi's sarcoma had disappeared. The lesions reappeared after eight months from the start of the program. This result shows that a relatively low amount of the invention can cause regression of cancerous lesions such those associated with Karposi's sarcoma.

Example 7

A 0.5 gram soft gelatin capsule containing 8 mg. DGLA and 80 mg. EPA. The number of capsules taken on a daily basis to modulate prostaglandins on a short term basis (up to 30 days) would be 4 capsules per day. The amount taken for a long term basis would be one capsule per day as less activated Omega 6 essential fatty acids are required to maintain tissue levels of DGLA to AA once they are established.

Example 8

Another example of a pharmaceutical composition of the invention is a physiologically compatible intravenous emulsion suitable for injection. 1.0 grams of purified soybean lecithin containing 75% phosphatidylcholine was dispersed in 100 ml. of distilled water buffered with 1 mM phosphate to pH 7.5. To the dispersed lecithin was added 10 grams of oil containing 1.2 grams EPA and 0.3 grams of GLA and 2.25 g of glycerine. The material was emulsified with a Branson W-375 sonifier under a nitrogen atomsphere. The resulting dispersion consisted of an emulsion with an average particle size of 261 nm.

Example 9

To illustrate an example of a food product containing the invention, a dairy emulsion suitable for food use can be made by the dispersion of 1.0 grams of a purified soybean lecithin fraction consisting of 45% phosphatidylcholine in 100 ml. of distilled water. To the dispersed lecithin is added 10 grams of oil containing 1.2 grams of EPA and 0.3 g GLA and 0.01 grams of artificial chocolate flavor. The mixture was homogenized and passed through a microfluidizing apparatus to produce a dispersion with an average particle size of 275 nm.

Example 10

To illustrate the potential of increasing the potency of the invention by fractionation of the active ingredients, in particular the GLA component, the following example is given. 500 g. of refined borage oil was refluxed for 1 hour with a solution of 400 ml. of ethanol, 125 ml. of water, and 115 g. of KOH. The mixture was cooled and 500 ml of crushed ice and 600 ml. of 0.4M $H_2SO_4$ was added. The layers were separated, and the upper layer was dried by the addition of 3% by weight of $MgSO_4$. At this point, the triglycerides of the borage oil have been transformed into free fatty acids. The $MgSO_4$ was filtered, and the free fatty acids are refluxed for 1 hour with 1000 ml. of methanol and 20 ml. of concentrated $H_2SO_4$. After cooling, 1500 ml. of water was added and phases were separated. To the upper phase containing the methyl esters of GLA was added 3% by weight of $MgSO_4$. The $MgSO_4$ was filtered and the solution was evaporated to dryness. At this point the concentration of the methyl esters of GLA relative to other fatty acids was 22.1% and the content of linoleic acid was 37.2%, which was similar to that found in the starting borage oil.

To further increase the potency of the methyl ester of GLA the following procedures were used. 1400 g. of urea was dissolved in 5600 ml. of warm methanol/ethanol (2:1 v/v). To the dissolved urea was added 500 g. of the methyl esters of GLA derived from borage oil. The mixture was placed at 0° C. overnight. The mixture was filtered and washed with cold methanol. To eliminate any urea that may have stayed in solution, to the filtered solution was added 1000 ml. of 0.4M $H_2SO_4$ for every 2000 ml. of filtered solution. The upper phase was separated and dried with $MgSO_4$. The $MgSO_4$ was filtered, and the solvent were evaporated under vacuum. From the starting 500 g. of unfractionated methyl esters of GLA, the yield was 96 g. Analysis of this fraction by gas liquid chromatography showed that the composition of this fraction was 92.4% GLA and 6.8% linoleic acid. The total recovery of GLA was 80.3%.

References

1. Lands, W. E. M. "Fish and Human Health" Academic Press, New York. (1986)
2. "Prostaglandin $E_1$ in Atherosclerosis" H. Sinziner and W. Rogtti eds. Springer-Verlag, New York (1986)
3. Wood, D. A., S. Butler, R. A. Riemersma, M. Thomson, M. F. Oliver, M. Fulton, A. Birtwhistle, and R. Elton. "Adipose tissue and platelet fatty acids and coronary heart disease in Scottish men." Lancet ii 117-121 (1984)
4. Horrobin, D. F. "Lowering of plasma cholesterol levels by essential fatty acids." in Clinical Uses of Essential Fatty Acids. D. F. Horrobin ed. Eden Press, Montreal pp. 89-96 (1982)
5. Sim, A. K. and A. P. McCraw. "The activity of gamma linolenate and dihomo gamma linolenate methyl esters in vitro and in vivo on blood platelet function in non human primates and in man." Throm. Res. 10 385-397 (1977)
6. Brenner, R. R. "Nutritional and hormonal factors influencing desaturation of essential fatty acids." Prog. Lipid Res. 20 41-48 (1982)
7. Adam, O. "Polyenoic fatty acid metabolism and effects on prostaglandin biosynthesis in adults and aged persons." in Polyunsaturated Fatty Acids and Eicosanoids. W. E. M. Lands ed. J. Amer. Oil Chem. Soc. Press. Champaign, IL. pp. 215-221 (1987)
8. Stone, K. J., A. L. Willis, M. Hart, S. J. Kirtland, P. B. A. Kernoff, and G. P. McNicol. "The metabolism of dihomo gamma linolenic acid in man." Lipids 14 174-180 (1979)
9. Hassar, B. A., Y. S. Huang, M. S. Manku, U. N. Das, N. Morse, and D. F. Horrobin. "The influence of dietary manipulation with n-3 and n-6 fatty acids on liver and plasma phospholipid fatty acids in rats." Lipids 21 652-661 (1986)
10. "Recommended International General Standards for Edible Fats and Oils." Codex Alimentarius Commission, World Health Organization. (1969)
11. Addison, R. F., M. E. Zinck, R. G. Ackman, and J. C. Sipos. "Behavior of DDT, polychlorinated biphenyls (PCB's), and dieldrin at various stages of refining of marine oils for edible use." J. Amer. Oil Chem. Soc. 55 391-394 (1978)

What is claimed is:

1. A method for the reduction of blood pressure levels in a hypertensive mammal, which method comprises administering to the hypertensive mammal a therapeutic, effective amount of a composition which consists essentially of in combination as the active ingredients:
   a) eicosapentaenoic acid (EPA) or a salt or ester thereof; and
   b) gamma linolenic acid (GLA) or a salt or ester thereof, the EPA and the GLA employed in a weight ratio of EPA to GLA of from about 2:1 to 8:1.
2. The method of claim 1 wherein said composition includes a carrier for the EPA and the GLA and which carrier is acceptable to the mammal.
3. The method of claim 1 wherein said composition comprises an emulsion.
4. The method of claim 1 wherein said composition is encapsulated in a soft gelatin capsule.
5. The method of claim 1 wherein said EPA compound is selected from the group consisting of: an EPA triglyceride; an EPA monoglyceride; and an EPA methyl ester.
6. The method of claim 1 wherein said GLA compound is selected from the group consisting of: a GLA triglyceride; a GLA monoglyceride; and a GLA methyl ester.
7. The method of claim 1 wherein the amount of the GLA comprises about 80 milligrams.
8. A method for the reduction of blood pressure levels in a hypertensive individual, which method comprises orally administering to the hypertensive individual a therapeutic, effective amount of a composition which consists essentially of as active ingredients:
   a) eicosapentaenoic acid (EPA);
   b) gamma linolenic acid (GLA); and
   c) a carrier for the EPA and GLA acceptable to the individual, the EPA and the GLA employed in a weight ratio of EPA to GLA of from about 2:1 to 8:1.

* * * * *